(12) United States Patent  (10) Patent No.: US 6,735,476 B2
Mellen  (45) Date of Patent: May 11, 2004

(54) ELECTRICAL STIMULATION DEVICE AND METHODS OF TREATMENT OF VARIOUS BODY CONDITIONS

(75) Inventor: Craig R. Mellen, Salt Lake City, UT (US)

(73) Assignee: S. Burt Chamberlain, Draper, UT (US)

( * ) Notice: Subject to any disclaimer, the term of this patent is extended or adjusted under 35 U.S.C. 154(b) by 0 days.

(21) Appl. No.: 10/319,364

(22) Filed: Dec. 14, 2002

(65) Prior Publication Data

US 2003/0114900 A1 Jun. 19, 2003

Related U.S. Application Data

(60) Provisional application No. 60/341,484, filed on Dec. 14, 2001.

(51) Int. Cl.[7] ................................................. A61N 1/18
(52) U.S. Cl. .............................. 607/46; 607/48; 607/50
(58) Field of Search ............................. 607/2, 72, 46, 607/48, 50, 51; 600/13–15

(56) References Cited

U.S. PATENT DOCUMENTS

| | | | |
|---|---|---|---|
| 4,119,102 A | * | 10/1978 | LeVeen ........................ 607/99 |
| 4,292,980 A | * | 10/1981 | Suzuki ........................... 607/2 |
| 4,349,030 A | | 9/1982 | Belgard et al. |
| 4,550,714 A | * | 11/1985 | Talish et al. ................... 600/14 |
| 4,641,633 A | * | 2/1987 | Delgado ....................... 600/13 |
| 4,646,744 A | | 3/1987 | Capel |
| 4,993,413 A | * | 2/1991 | McLeod et al. ................ 607/2 |
| 5,052,391 A | | 10/1991 | Silberstone et al. |
| 5,282,843 A | | 2/1994 | Freeman |
| 5,487,759 A | | 1/1996 | Bastyr et al. |
| 5,569,166 A | | 10/1996 | Stone |
| 5,620,463 A | | 4/1997 | Drolet |
| 6,023,642 A | | 2/2000 | Shealy et al. |
| 6,044,303 A | | 3/2000 | Agarwala et al. |
| 6,161,044 A | | 12/2000 | Silverstone |
| 6,167,304 A | * | 12/2000 | Loos .............................. 607/2 |
| 2001/0007949 A1 | | 7/2001 | Silverstone |

* cited by examiner

Primary Examiner—Jeffrey R. Jastrzab
(74) Attorney, Agent, or Firm—Mallinckrodt & Mallinckrodt; Robert R. Mallinckrodt

(57) ABSTRACT

An electrical stimulation device for applying electrical stimulus to a living body includes a pair of applicators adapted to each contact the living body. The applicators each include electrically conductive material covered by electrically insulating material whereby the electrically conductive material is separated from the living body by the electrically insulating material when the applicators contact the living body. A preferred applicator is formed of flat cable having a plurality of conductors therein that form a plurality of antennas for transmitting electrical signals to the body. A signal generator generates a series of positive electrical pulses to be applied to the living body through the applicators. The applicators of the invention allow much more power to be applied to the body than is possible with prior art devices and the signal generator allows a user a wide range of power adjustment so that the intensity of the signal applied to the body can adjusted over a wide range to obtain desired intensity effects. The device can be used for treating and creating a wide range of body conditions such as treating pain and related stress and bleeding and blood clots, stimulating muscles, finding microorganisms, and treating UV skin damage.

20 Claims, 6 Drawing Sheets

Figure 1:
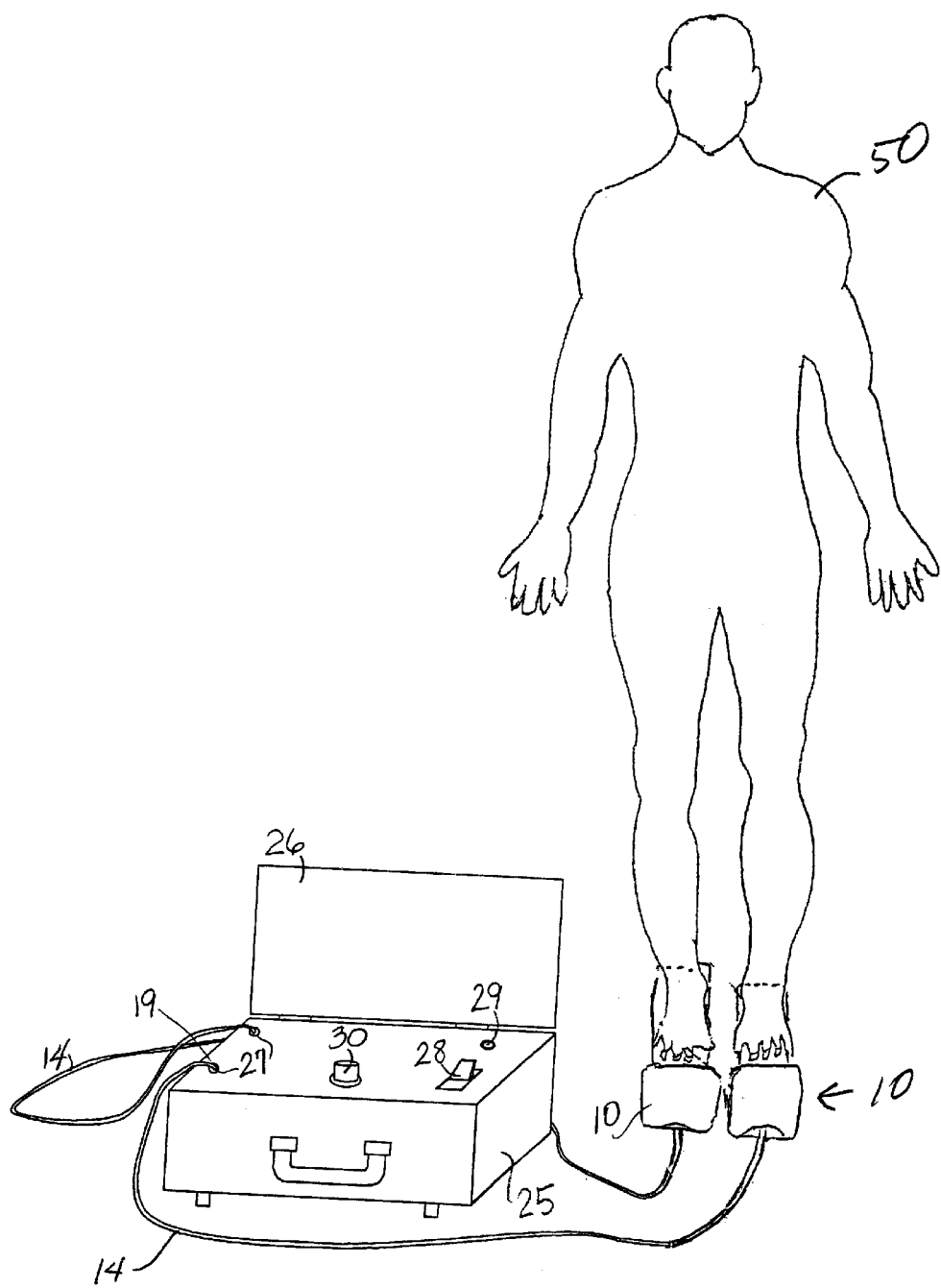

ELECTRICAL STIMULATION DEVICE AND METHODS OF TREATMENT OF VARIOUS BODY CONDITIONS

RELATED APPLICATION

This application claims the benefit of provisional Application Serial No. 60/341,484, filed Dec. 14, 2001, and entitled: "Electrical Stimulation Device."

BACKGROUND OF THE INVENTION

1. Field

The invention is in the field of devices for applying electrical signals to a living body and to methods of treating body conditions and producing reactions and conditions in living bodies by means of applying electrical signals to such bodies.

2. State of the Art

There are currently various kinds of electric stimulators and methods of applying electrical signals to a body available for the purpose of managing pain and its associated stress, stimulating muscle function, and for treating various medical and other body conditions and/or the symptoms thereof. The stimulators and methods of the prior art are usually referred to in catagories recognized by the acronyms: TENS (Transcutaneous Electrical Nerve Stimulation), MENS (Microvolt Electrical Nerve Stimulation), and EMS (Electric Muscle Stimulation).

When the application of electrical signals are directed to the treatment of pain, the equipment and methods used are usually referred to as TENS (Transcutaneous Electrical Nerve Stimulation) systems. It is claimed that such systems are able to stimulate specific nerves to ease pain at a specific point in a body.

There are two major theories explaining how electric stimulation relieves pain. According to the first theory, the—"gate control theory,"—pain and non-pain impulses are sent to the brain from the local nervous system. These pulses travel through the cutaneous (surface nerves) to the afferent (deeper) nerves and then to the spinal cord and brain. Along the path are many areas referred to as "gates." These gates determine which impulses are allowed to continue to the brain and thus prevent the brain from receiving too much information too quickly. Also, since a single nerve cannot carry a pain impulse and a non-pain impulse simultaneously, it is said that the stronger, non-pain impulse from the TENS device "controls the gate" and keeps the body form feeling the pain.

According to the second theory, TENS stimulation encourages the body to produce natural pain killing chemicals called endorphins. These chemicals are said to interact with neuron receptors in such a way as to block the perception of pain. The effect is much the same as that of the pharmaceutical drug morphine but without the side effects associated with use of the drug.

TENS units use carbon rubber electrodes that can be affixed to the skin in various ways, such as with adhesive tape. These electrodes deliver bursts of electrical current through the coetaneous surface skin in contact with the electrodes to the afferent (deep) nerves for the purpose of controlling pain. However, since these electrodes have direct contact with the skin there is an inherent problem. Direct contact between the electrodes and the skin can induce paresthesia, (a tingling sensation) that can cause feelings of heat or burning—even the point of feeling like being electrocuted. These and other forms of discomfort are present depending upon the current flowing from the electrodes into the skin. The current flow depends upon the strength of the signal applied to the electrodes and the power contained in the signals. Thus, unless the current is delivered at very low level, the experience can become very uncomfortable and at times extremely painful and stressful. The amount of power that can be applied to a body through electrodes in direct contact with the skin of the body is generally in the range of about ten to twelve watts. Power levels above that cause to much current flow from the electrodes into the skin in contact with the electrodes and are painful.

Another problem with prior art TENS devices are that they deliver a bipolar waveform that is not truly compatible with the digital, polar signals produced by the human and other living bodies.

MENS (Microvolt Electrical Nerve Stimulation) devices have been described for use as electro acupuncture devices. MENS devices deliver an electric pulse approximately three orders of magnitude less than a TENS device. With lesser voltage and wattage, the signal is less likely to burn. Also, the MENS signal, when delivered through the acupuncture points, tends to be more "physiologic" in that it mimics the body's electric signals. Those who are skilled in the art are now tending to believe that physiological compatibility is important.

With the MENS systems, however, the needles form direct electrodes in contact with tissue. Thus, this combination of the needles and the electric current can still become more of a torture than a treatment. It can be very uncomfortable depending on the voltage used to drive the signal. In fact, since the needles create much smaller electrodes than the electrodes generally placed on the skin, much smaller signal are necessary to avoid discomfort. Another concern is that the prior art MENS devices actually deliver a bipolar waveform that is not truly compatible with the digital, polar human body. In addition, a skilled acupuncturist is necessary to place the needles, thus making it impossible for a user to use the device his or her own.

EMS (Electric Muscle Stimulation) uses electro stimulation to sooth muscle aches and pains, provide electro muscle massage, and to tone muscles and build muscle mass. Normal neurological control of muscle contraction (tetanus) is accomplished with positive electrical signals produced by the body. EMS provides a mechanism and the means for causing contraction of muscles using an external stimulus (artificial tetanus). However, prior art EMS (Electric Muscle Stimulation) teaches the use of bipolar waveforms. In addition, electrodes are used which again limit the amount of current and power that can be applied to the body.

Many of the prior art TENS, MENS, and EMS devices allow the operator to vary the frequency and intensity of the signal applied to the body during a treatment session. Some of the prior art devices even automatically vary the frequency and intensity of the signal as part of the treatment. This appears to cause confusion within the body when it has to constantly adapt from one signal to another and does not appear to be beneficial.

SUMMARY OF THE INVENTION

According to the invention, electrical signals can be introduced into the body using applicators that generate a current flow in the body but do not cause current to flow directly from the applicator into the body. This allows higher levels of power to be applied to the body without the burning and feelings of electrocution that accompany high power levels using conventional electrodes where current flows directly from the electrode through the skin into the body. The applicators of the invention include electrically conductive material covered by electrically insulating material which contacts the body to prevent direct body contact with the electrically conductive material. It has been found that a length of multiconductor flat or ribbon cable such as used in internal computer connections between circuit boards or cards works very well. Each of the individual conductors or wires in the cable appears to form an antenna for transmitting power into the body, and is more efficient than a single conductive plate. Preferred applicators are relatively large with surface areas of up to about 120 square centimeters. Power densities of up to about one watt per square centimeter can be used with no discomfort to the recipient. This means that with a 120 square centimeter applicator surface, up to about 120 watts of power can be comfortably applied to the body. It has been found that the intensity of the signal applied to the body is important. Higher intensity signals appear to provide better therapeutic results, although it is usually preferred to build up to the higher intensity signals.

A further significant aspect of the invention is the use of positive pulses to cause generation of the electrical signals in the body rather than bipolar (AC) signals. The natural neurological signals in the body are positive signals, not AC signals. Therefore, using positive signals rather than AC signals more closely mimic the natural body signals and creates signals within the body that are more compatible with and accepted by the body than AC signals. While pulse frequencies from about 1 to 10,000 hertz can be used, pulse frequencies in the range of about 40 to 100 hertz have been found preferable. Frequencies below about 40 hertz tend to make a person sleepy while frequencies above about 100 hertz tend to make a person feel somewhat on edge or uncomfortable. It is preferred that the pulse width be between about 0.5 and 1 millisecond, and the signals may range in voltages up to about 20,000 volts. Power applied may range up to about 120 watts The electrical stimulation device of the invention can be used wherever prior art electrical stimulation devices are used and generally with the increased power of the signals generated and the purely positive pulses used, have been found to be more effective in such uses than the prior art devices. The stimulator of the invention can be used very effectively for the treatment of pain and related stress, such as from headaches, arthritis, injuries such as back injuries, carpal tunnel syndrome, or other causes, and has been found to help in the healing of such conditions. It can be used for muscle stimulation for muscle development and rehabilitation. It has been found that it can be used for finding and identifying microorganisms within a body where once the organisms have been identified, they are attacked by and destroyed by the body's own immune system. It has also been found that use of the device can slow or prevent bleeding and bruising, can break down blood clots, and is effective in reversing skin damage from sun exposure.

THE DRAWINGS

Figure 2:
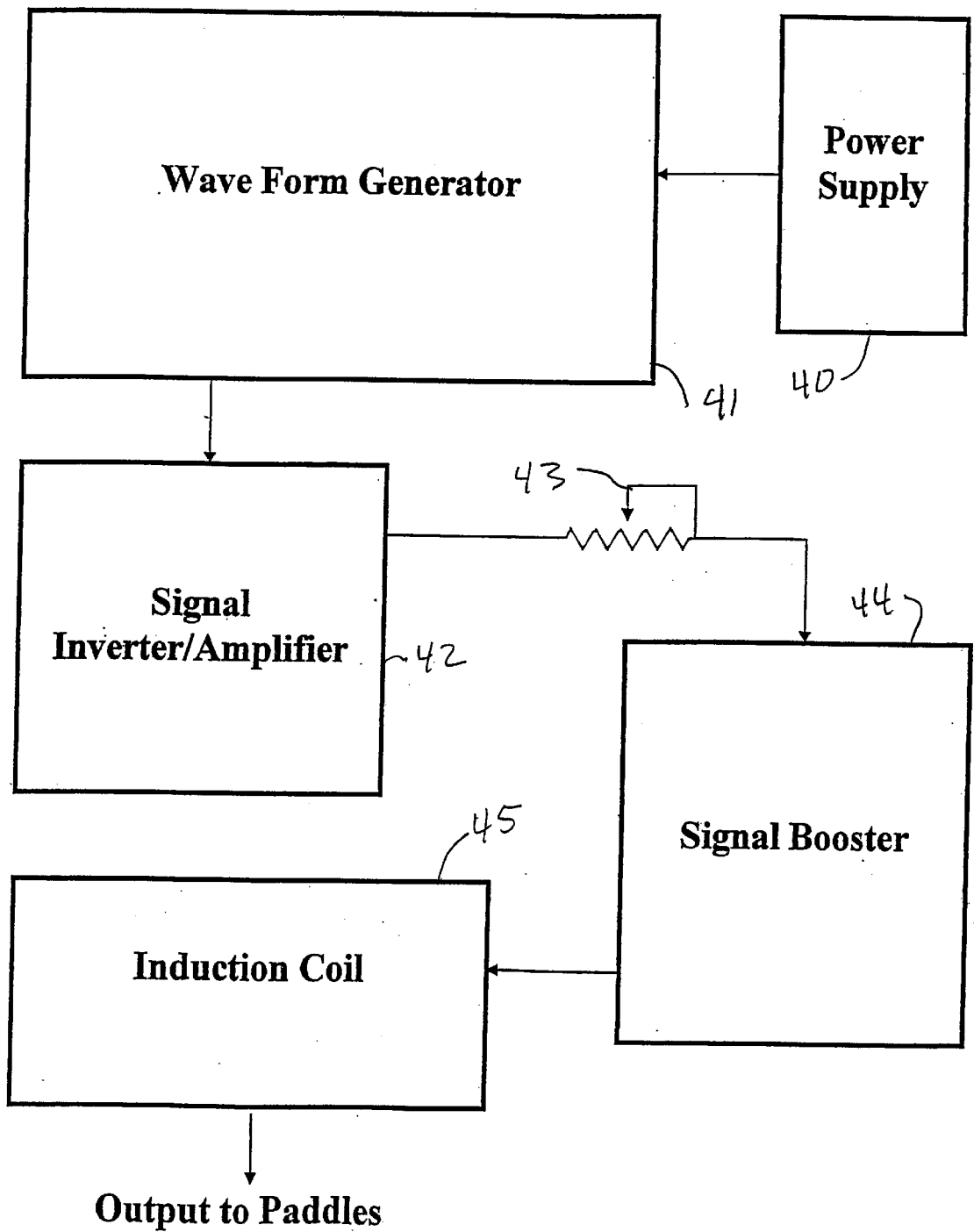
Figure 3:
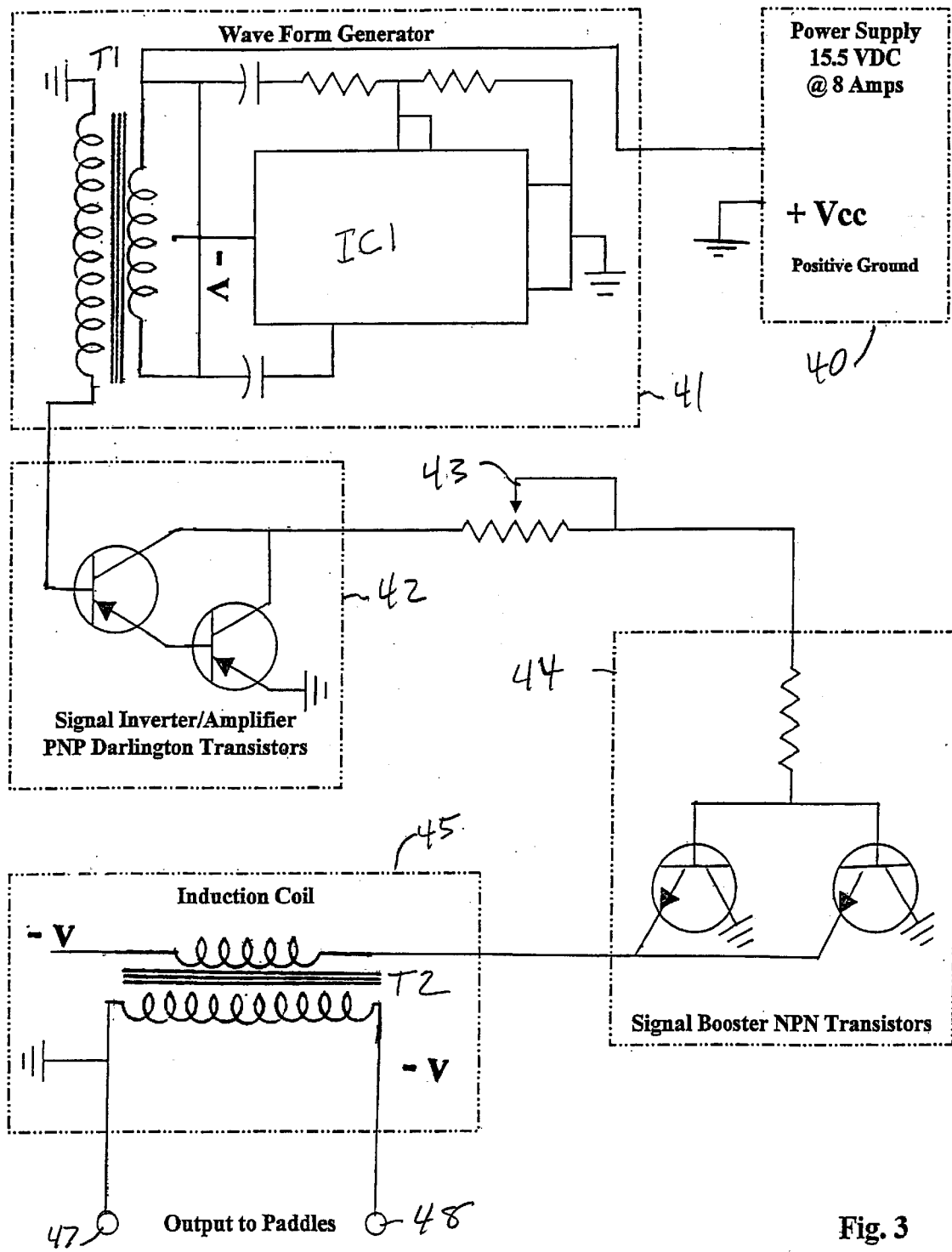
Figure 4:
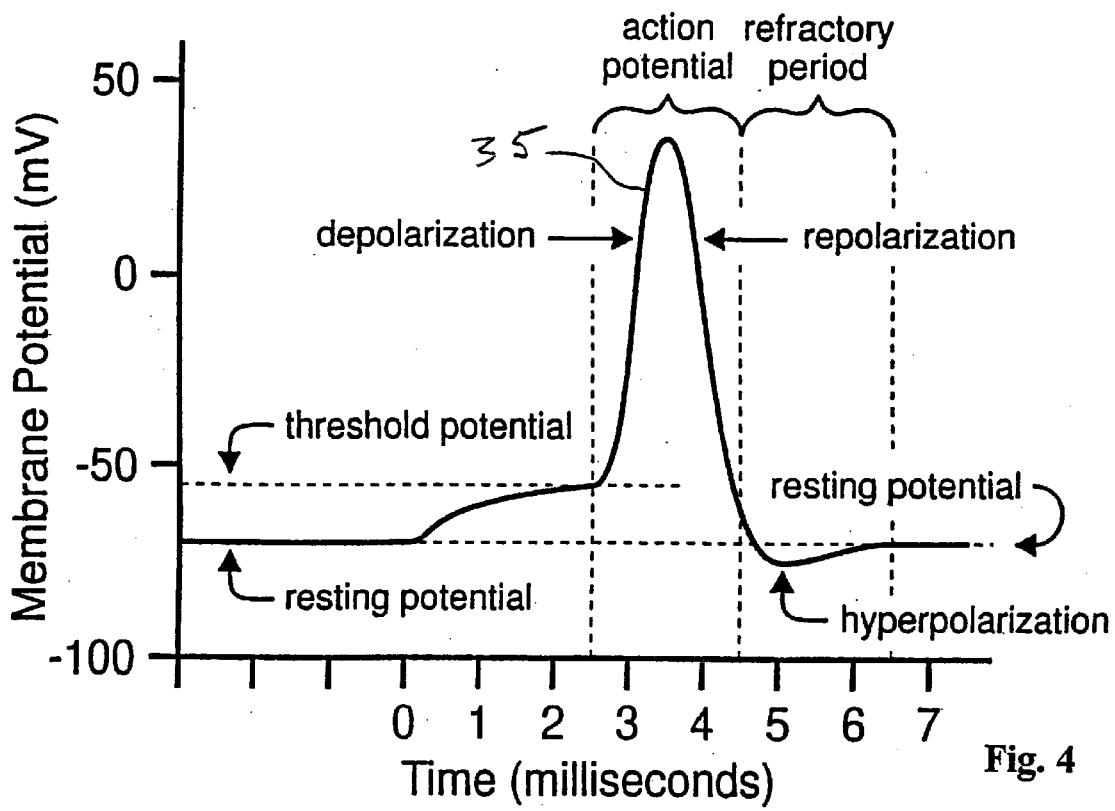
Figure 5:
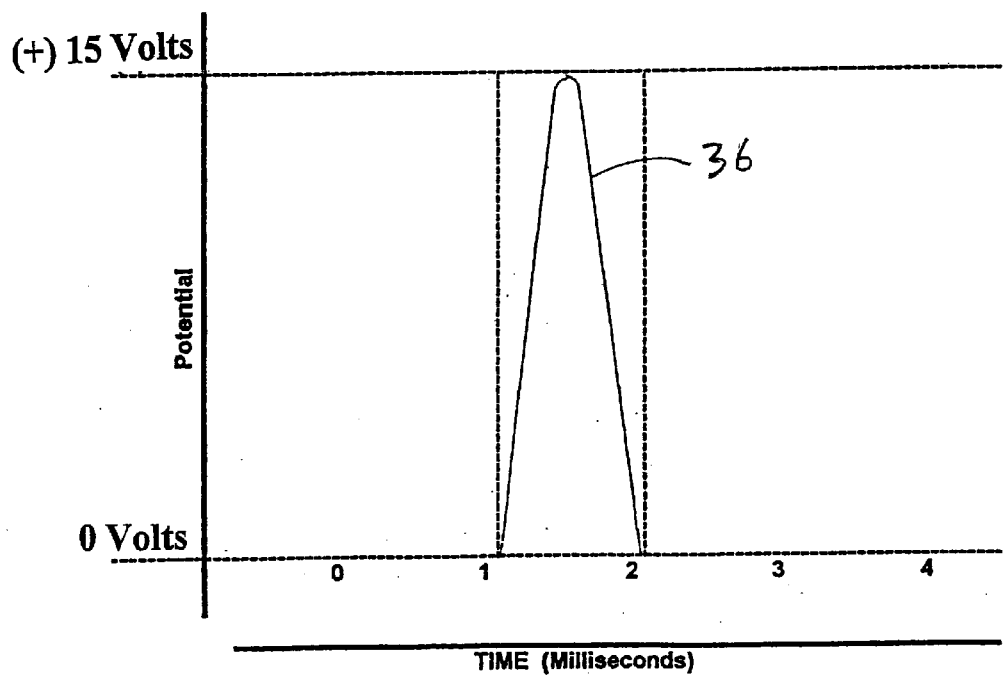
Figure 6:
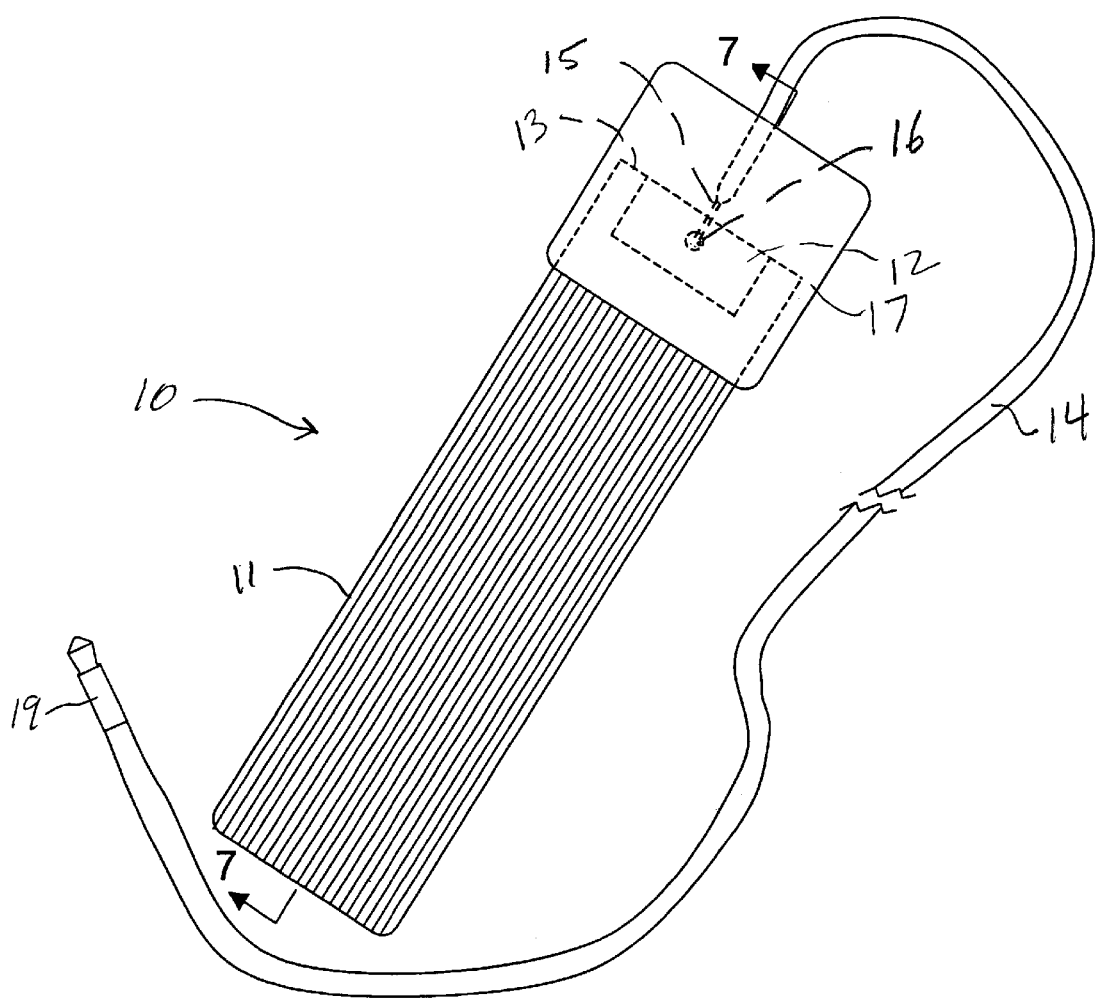
Figure 7:
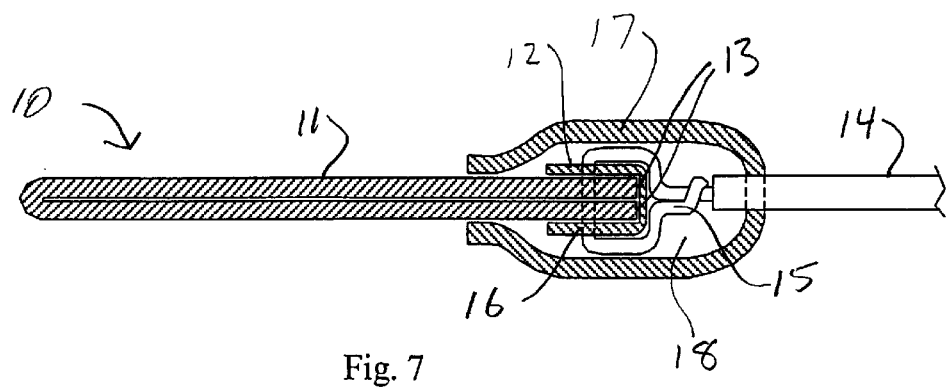
Figure 8:
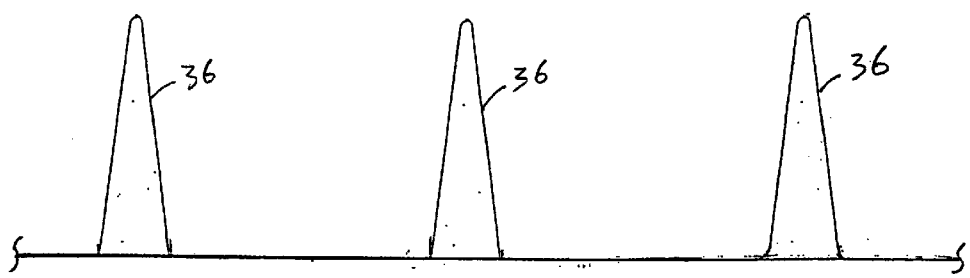

In the accompanying drawings, which show the best mode currently contemplated for carrying out the invention:

FIG. 1 is a perspective view showing one possible connection between the device of the invention and an individual;

FIG. 2, a block diagram of a preferred signal generator of the invention used in accordance with the methods of the invention;

FIG. 3, a circuit diagram of various blocks of the preferred signal generator of the invention as shown in FIG. 2;

FIG. 4, a diagram of the natural, neurological synapse waveform as it occurs in the body;

FIG. 5, a diagram of the facsimile of the signature waveform supplied by the signal generator;

FIG. 6, a top plan view of an applicator of the invention;

FIG. 7, a vertical section taken on the line 7—7 of FIG. 6;

FIG. 8, a representation of a preferred pulse waveform of the invention; and

Figure 9:
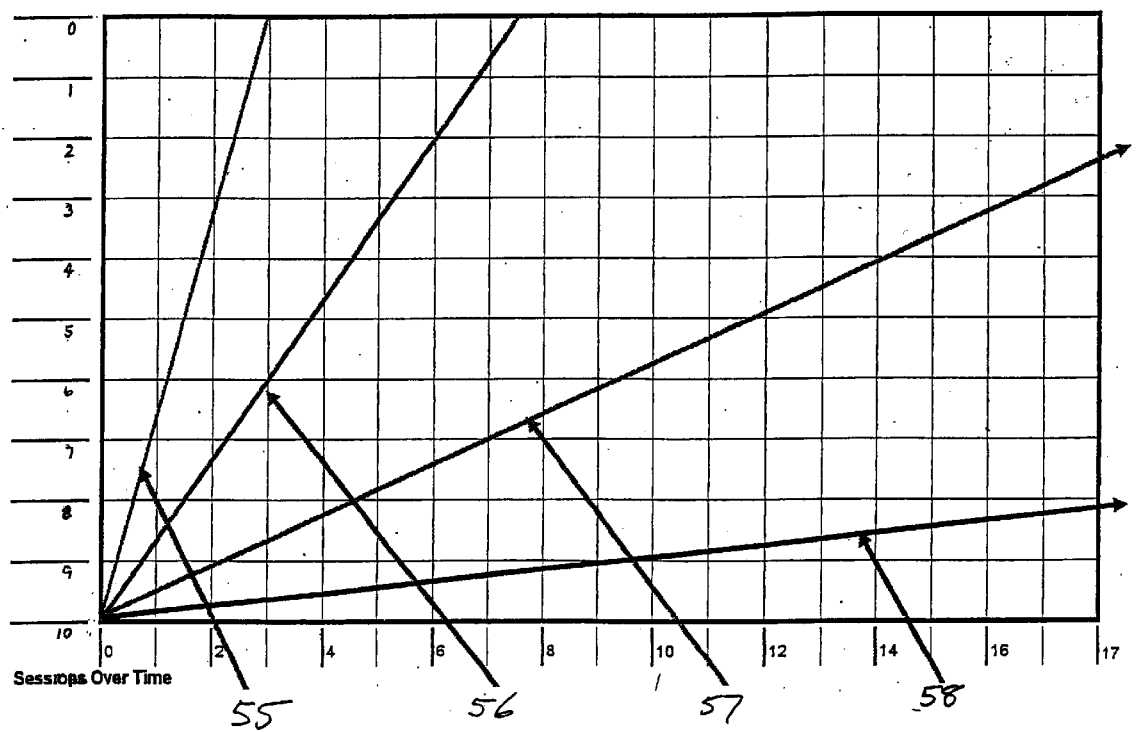

FIG. 9, a graphical presentation of pain reduction experienced through treatments using the device and methods of treatment of the invention.

DETAILED DESCRIPTION OF THE ILLUSTRATED EMBODIMENTS

An important aspect of the invention is to provide applicators for creating electrical signals in a living body and electrical current flow in the body without causing current to flow directly from the applicator through the skin into the body of from the body through the skin into the applicator. Prior art devices provide electrically conductively electrodes where current flows from the electrically conductive electrode placed in contact with the skin, through the skin, and into the body. This arrangement limits the power of the signals applied to the body because the current passing through the skin can cause a burning sensation and discomfort to the user. In some situations, conductive cream or liquid is placed on the skin between the electrode and the skin to try to increase the current that can be used by decreasing the electrical resistance of the skin at the interface.

The applicator of the invention prevents direct current flow from the applicator through the skin by providing an insulating material between the electrode, i.e., the electrically conductive material, and the skin which prevents such direct current flow. As shown in FIGS. 6 and 7, a preferred applicator 10 of the invention is fabricated from a length of flat or ribbon cable 11. Flat or ribbon cable includes a plurality of individual insulated wires joined in side-by-side configuration to form a substantially flat, multiconductor cable. The width of the cable depends upon the number of side-by-side conductors or wires. A flat cable with about forty individual wires is satisfactory and will be about two inches wide. A twenty four inch long flat cable 11 can be bent over on itself as shown in FIG. 7. A conductive tape 12, such as aluminum tape, is folded over the adjacent ends 13 of the folded cable 11, and a wire 14 is connected to the tape 12 in any suitable manner, such as by passing the striped, conductive end portion 15 of the wire over the tape 12, through a hole 16 through the tape 12 and cable 11, and twisting it back on itself. A nonconductive pocket 17, such as made from a silicone material, is secured over the end of the cable and the conductive tape, such as with a silicone adhesive that can be dried or heat cured, to form a durable applicator. The silicone adhesive will fill area 18 in pocket 17 around the ends 13 of the cable, the conductive tape 12, and connecting wire 14. The length of the flat cable portion extending from the pocket will be about nine inches. Rather than folding the cable back on itself, a single straight length of cable can be used with the end of the cable away from the connection with connecting wire 14 also covered with a nonconductive pocket. The end of connecting wire 14 opposite its connection with applicator 10 is provided with a plug 19 or other connector for connection to a signal generator.

It has been found that use of the flat cable which provides about forty individual wire conductors or antennas works well. The output of a solid flat conductive material has been found to be only about 25% as effective and efficient as the multiple conductors. Further, it has been found that flat cable with silver-copper alloy wire is more effective than pure copper wire. The number of conductors in the flat cable is not critical, as long as a plurality of conductors is present, and will be chosen to provide an applicator of a desired width.

While the construction of the applicator shown in FIGS. 6 and 7 has been found satisfactory, various other applicator constructions can be used. The important feature of the applicator is that conductive material that is connected to receive signals from a signal generator is covered with insulating material so that there is no direct contact between the skin and the conductive material.

The signal generator of the invention may take various forms and may be supplied in a portable case 25, FIG. 1, with top 26. Since two applicators are necessary to generate electrical signals in a body just as two electrodes are necessary in the prior art machines, two receptacles 27 are provided to receive plugs 19 from two applicators 10. An on/off switch 28 to turn the signal generator on or off, a power on indicator light 29, and an intensity control 30 to vary the intensity of the signal supplied to the applicators are also provided.

While the applicators of the invention may be advantageously used with signal generators of the prior art or with signal generators that produce bipolar (AC) signals of the prior art, a feature of the invention is the use of a special positive pulse or digital signal that is similar in shape and duration to the body's natural neurological signals. The body's natural neurological signal is shown in *CliffsQuickReview Anatomy and Physiology*, 2001 Edition, by Phillip E. Pack, published by Hungry Minds, Inc., incorporated by reference herein, Page 118, as shown in FIG. 4. The signal of FIG. 4 represents what is referred to as "the action potential," the actual signal used by the human nervous system. I have found that the positive portion of the signal 35, i.e., the portion of the signal that is above zero potential labeled "polarization and depolarization," is the only part of the signal that is needed to cause a positive effect in the body and is the only portion of the signal that is active or causes "action." I have also found that the closer the signal actually applied to a body is to this natural signal, the better the acclimation or accommodation for the person receiving therapy. I believe that this is "a" preferred signal for electrical signals applied to the body because it is the one that mimics the naturally occurring signal. FIG. 5 shows my preferred signal 36 as generated by my preferred signal generator. As can be seen, this is a close representation of the positive portion of the body's natural signal shown in FIG. 4. The duration of both signals is in the range of 0.5 to 1 millisecond. I generate the signals 36 with a repetition rate to provide a desired frequency. FIG. 8 shows several of the repeated signals or pulses 36. The time between the signals or pulses determines the frequency of pulses or signal frequency. While pulse frequencies from about 1 to 10,000 hertz can be used, pulse frequencies in the range of about 40 to 100 hertz have been found preferable. Frequencies below about 40 hertz tend to make a person sleepy while frequencies above about 100 hertz tend to make a person feel somewhat on edge or uncomfortable. The higher frequencies seem to create stress and hypertension in the person being treated. A frequency of between fifty and sixty cycles seem to stimulate the person being treated while being comfortable. My preferred frequency is about fifty seven hertz because it falls within the preferred range and is an efficient frequency for operation of the iron core induction coil used in the signal generator.

As shown in FIGS. 2 and 3, power is supplied by power supply 40 to a wave form generator 41 as well as to other parts of the circuitry not indicated. The wave form generator 41 produces the signature signal shown in FIG. 5. As produced by the wave form generator 41, the signal is a fifteen volt, five hundred milliamp signal. This signal is inverted and amplified in signal inverter/amplifier 42 and then passes through a potentiometer 43 which controls the level or amplitude (intensity) of the final output signal. The signal is again amplified in the signal booster 44 and is passed through an induction coil 45 to produce an high voltage output signal that is applied to the applicators, which are also referred to as paddles.

The circuit blocks are shown in more detail in FIG. 3. The power supply may be any standard power supply, such as a transformer power supply with a 120 volt AC input from a standard electrical wall receptacle, that produces an output of about 15.5 volts at eight amps. The power supply is connected to provide the circuit with a positive ground. The power supply is not shown in detail. A power on/off switch is included in association with the power supply. The power supply 40 is connected to the wave form generator 41. The wave form generator is standard wave form generating circuitry using a 555 timer IC1 and a transformer T1. The output of the waveform generator is the signal of FIG. 5. The signal inverter/amplifier circuitry 42 is a Darlington pair of PNP transistors. A pair of NPN transistors form the signal booster circuitry 44. The boosted signal is sent to an automotive ignition induction coil T2 to generate the output signal of the signal generator that is connected to the applicators or paddles. This final output signal appears across the two terminals 47 and 48 and is a series of positive pulses of shape similar to that of FIG. 5, connected as in FIG. 8, and adjustable by potentiometer 43 to up to 20,000 volts.

The signals can be applied to a person being treated in various ways. FIG. 1 shows the person 50 being treated standing with bare feet with one foot on each of the two applicators. Electrical signals are generated in the body to travel up one leg and down the other. Such arrangement can be used, for example, to treat ankle and knee pain such as caused by arthritis, and to help in healing damage to those joints done by the arthritis. The applicators could be held in opposite hands to send signals through the hands, wrists, elbows, shoulders, and arms to treat those joint and body parts. The applicators can be placed on the temples of the head to treat the head and brain. The applicators may be placed in spaced relationship along the back to treat a back injury or on the neck to treat a neck injury. Various placements can be used depending upon the body part or parts to be treated. The applicators may be of various sizes and configurations and may include straps for holding the applicators in position against certain body parts. It is currently preferred, as indicated in describing the applicator construction, that the applicators be about nine inches long and about two inched wide. This gives a surface area of the applicator that can be placed in contact with the skin of about 120 square centimeters. It has been found that a signal of up to about 120 watts can be comfortably used with such applicator giving a power density of about one watt per square centimeter of applicator surface.

The invention can be used as with EMS devices to activate muscles for exercising the muscles. Muscle contraction is accomplished by a number of steps. The major event involves the action potential where the neuron secretes the neurotransmitter acetylcholine (Ach), which diffuses across the synaptic cleft. This appears to be happening in response to the applied signal. As the intensity of the applied signal increases, the muscle goes from a condition of incomplete (unfused) tetanus to a condition of complete (fused) tentanus. This phenomenon works very well by using the constant frequency signal and varying the intensity alone, without changing the frequency. The signals of the invention provide stronger muscle control and reduced pain. It produces strong control of the muscles and causes production of natural endorphins to inhibit pain.

The device of the invention also can also be used as with prior art TENS machines to reduce pain. Application of the electrical signals to the body have been found effective to reduce a wide variety of pain. Pain is difficult to measure. Those who a try to assess pain and distress levels rely on subjective reports provided by patients by asking them to assign a number between one and ten with one meaning there is no pain and ten meaning that the pain is as intense as it possible could be. This ten point scale is referred to as the Subjective Units of Distress Scale (SUD). The graph of FIG. 9 shows the results of tests conducted with the device of the invention in the treatment of several types of pain. The graph shows the average results obtained by individual users over the past two years and comes from interviews with users rather than actual before and after SUD ratings per se.

The vertical axis represents improvement in SUD ratings as a result of stimulation. The horizontal axis shows number of stimulation sessions over time. Four conditions of concern have been plotted on the chart: Headaches both migraine and others, Carpal Tunnel Conditions, Recent Back Injury, and Arthritic type problems.

The results of treating migraine and other headaches is shown by line 55. Migraine and other headaches are generally eliminated with three twenty minute sessions of stimulation with a twenty minute rest or nap period after each stimulation. This translates into about 1-½ hours total stimulation. Generally the condition does not return within 6 months and if it does return it can be eliminated in even less time. The results show the average for fifty people treated.

The results of treating carpal tunnel type conditions is shown by line 56. Stress from carpal tunnel conditions take about fifteen to twenty minutes of stimulation once a day for seven to ten days. The results show the average for fifty to one hundred people treated.

The results of treating recent back injuries is shown by line 57. Most recent back injuries will require approximately twenty to thirty minutes of stimulation twice a day for six to eight days. Old injuries will take longer. The results show the average for twenty-five to fifty people treated.

The results of treating arthritic type conditions is shown by line 58. Arthritic conditions generally require approximately thirty minutes of stimulation, once a day for about six weeks. Long standing conditions may take longer.

It has been found that the signals of the invention can supplement normal body reactions to create stronger vasoconstriction to stop bleeding and lessen bruising. Vasoconstriction is initiated by the smooth muscle of the blood vessel. These smooth muscles of the blood vessel can be artificially stimulated by the signals of the present invention to lead to stronger vascular constrictions. The signals acts like ice—ice causes constriction of blood vessels and works as a pain inhibitor by slowing down chemical reactions by refrigeration. It also slows down the bleeding from a wound. However, it has been found that with application of electrical stimulation, at low intensities of the electrical stimulating signal the bleeding from a wound increases. But, at higher intensities of the signal, the bleeding slows down and stops. The electro stimulus from the invention at high enough intensities works approximately 2 to 3 times better than ice as a non-invasive way to prevent bruising and pain. Another point is that the signal also accelerates the adhesion of platelets.

The signals of the invention can also help in fibrinolysis—the breaking down of a blood clot as the damaged blood vessel is repaired. The mechanics starts with the production of the plsminogen activator (t-PA) which converts plasminogen into its active form, plasmin (figrinolysin). Plasmin, in turn, breaks down fibrin and leads to the dissolution of the clot. When the stimulation of the invention is applied, this process happens very rapidly, even to the point that one can see black and blue bruises disappear. One can see the black and blue areas changing to red splotches and then from red splotches to a healthy pink. As this is happening, the pain is greatly reduced. This can provide treatment for stroke victims who have paralysis and speech impairment due to clotting in the brain because of fibrinogen. Extrinsic clots (clots outside the blood vessels) are extremely hard to get rid of, and they cause a great deal of damage and slowing of healing. These clots surround the damaged area, prevent healing and cause inflammation and swelling making the tissue more vulnerable to infection. The invention works to get rid of these clots.

The invention can be used to find and stimulate microorganisms in a body thereby causing the microorganisms to be discovered and destroyed by the body's immune system. Microorganisms have propulsion systems that are similar to muscles; they also have glandular functions that produce pain toxins and poisons. They appear to cramp up in a manor that seems to mimic involuntary muscle contractions and this cramping causes them to involuntarily excrete pain toxins and poisons into the body. The pain, or increased pain, caused by these excretions tells the individual exactly where they are, thus identifying the point where stimulation is needed. Also, the involuntary secretions seems to "blow their cover" and alert the immune system to their presence, thus allowing the immune system to mobilize its defenses and effectively take them out.

This theory is supported by the following experiment. Many individuals have a low-grade infection in their sinus cavities. Usually such an infection will be contained in an epicenter approximately ½" to 1" in diameter. According to the theory, there would be little or no pain associated with this particular colony since it appears that the microbes are in a colony-building phase and want to avoid detection.

Now introduce the electromagnetic signal of the stimulator by holding one paddle across the forehead just above the eyes with the other paddle contacting the body at any other location on the body and turning up the amplitude slowly. When the signal gets strong enough, where this little colony is located, the individual will begin to feel pain. According to the theory, this pain is caused when the organisms are tricked into involuntarily squeezing out some of their pain toxins and poisons. By doing this, they have exposed themselves and their location is obvious because of the pain they caused. Not only, is their location known to the individual, but also, the immune system is alerted to their presence because of their chemical pollution.

In this scenario, with the paddle across the forehead the individual will only feel pain at the hypothetical colony location since, by definition, there were no other microorganisms in the sinus cavity to be squeezed. When the paddle is removed from the forehead, the pain will still be there but will soon subside because there is no longer an electrical stimulus to cause the phenomenon.

The evaluation of the experiment is that:

The pain did not come from the body. There was no pain before applying the signal and there was none after the signal was removed.

The signal did not cause the pain. Where there was no colony in other parts of the sinus there was no pain and there was no pain in other parts of the forehead even though the signal was applied across the entire forehead.

Before the experiment, the microorganisms did not produce pain. Therefore, it appears that the pain did not come from the microorganisms per se, rather, it was the result of the stimulation. By definition, they were there before the experiment and no pain was felt. They were there after the experiment and still no pain was felt. To determine if the organisms are still present or not, just apply the signal again and the pain will return but at a reduced level. One probable explanation of this reduction is that the immune system attacked the organisms that secreted the toxins.

Did the signal kill the pathogens? No. It is believed that the best possible explanation is that the signal caused the microorganisms to involuntarily squeeze out some of their toxins and poisons. This alerted the immune system to send in the antibodies to destroy the polluting pathogens.

The nature of the electron transmission between the applicators or paddles and the body involves high ion potentials that appear to create ionized oxygen and nitrogen molecules in the gap between the skin and the paddle—an aurora like phenomenon. This particular aurora creates a glow of mostly ultraviolet light. A small part of the violet light is visible and can be seen. But, of more particular importance is the fact that this UV radiation is super-mild and has the ability to reverse the more powerful UV radiation damage that typically comes from sunlight. In other words, the phenomenon is that that sunlight UV damage is reversed or neutralized by the more mild form of low energy UV light that is created artificially through the electrical ionization of ordinary air.

One case scenario that backs up this claim is that of the inventor who as a roofing contractor spent 35 years working in the out doors. His neck, ears and arms we sunburned repeatedly and received a great deal of UV damage. After applying the low level UV energy from the device, his dermatologist was really surprised to see the reversal of almost all of the UV damage that had been caused by many years of exposure. For the most part, UV damage is collective and not reversible except by laser treatment and other forms of expensive medical procedures. This treatment is fighting damage caused by high level UV radiation with the application of low level UV radiation. I call this fighting fire with fire.

An article in the February, 1999 issue of *Scientific American* entitled "How Limbs Grow," incorporated herein by reference, points out that different concentrations of a growth-regulating gene can have opposite effects on the growth of the body. For example, at one concentration of a particular gene, arms and the hand may grow at one rotational orientation to form, for example, a right hand. At a different concentration of the same gene, the arms and hand will grow at a different rotational orientation to form, for example, a left hand. Thus, opposite results are encountered depending upon the concentration of a particular substance, called by the authors "the concentration effect." The same thing appears to apply with the intensity of electrical signals applied to a body. This I call "the intensity effect." The present invention allows a wide adjustment in the intensity of the electrical signals applied to a body so the desired intensity effect can be achieved.

The authors of the Scientific American article state: "once a molecular signaling pathway is established, nature often finds ways to use it in many other settings." With the current invention, I have established a signaling pathway produced electronically instead of molecularly. This signaling pathway can be used in many different settings, such as, for example: the firing of motor neurons with the (Ach) complex; controlling pain with inhibitors (IPSP) or exciters (EPSP)—endorphins; the control of coagulation of the blood with the plsminogen activator (t-PA); the control of UV damage with the fire fighting fire principle; and detection and control of microorganisims. These are examples of five separate pathways using the same signal. The pathway used is determined by the location of the stimulus and the intensity of the signal.

Whereas the invention is here illustrated and described with reference to embodiments thereof presently contemplated as the best mode of carrying out the invention in actual practice, it is to be understood that various changes may be made in adapting the invention to different embodiments without departing from the broader inventive concepts disclosed herein and comprehended by the claims that follow.

I claim:

1. An electrical stimulation device for applying electrical stimulus to parts of a living body comprising:

a pair of applicators adapted to each contact the living body, said applicators each including electrically conductive material covered by electrically insulating material whereby the electrically conductive material is separated from the living body by the electrically insulating material when the applicators contact the living body;

a signal generator having a pair of output terminals and adapted to generate an electrical signal between the output terminals to be applied to the living body through the applicators, wherein the electrical signal is a series of positive electrical pulses with a frequency in the range of 40 to 100 Hertz and has a voltage in the range of 10,000 to 20,000 volts and electrical conductors connecting respective separate terminals of the pair of signal generator terminals to respective separate applicators of the pair of applicators to supply the electrical signal generated by the signal generator to the applicators.

2. An electrical stimulation device for applying electrical stimulus to parts of a living body according to claim 1, wherein the power applied by the signal generator to the electrodes is adjustable up to about 120 watts.

3. An electrical stimulation device for applying electrical stimulus to parts of a living body according to claim 2, wherein the power applied by the signal generator to the electrodes is adjustable in the range of about 5 to about 120 watts.

4. An electrical stimulation device for applying electrical stimulus to parts of a living body according to claim 3 wherein the duration of each positive electrical pulse is about 1 millisecond.

5. An electrical stimulation device for applying electrical stimulus to parts of a living body according to claim 4 wherein the electrodes are each formed from a length of insulated, multiconductor ribbon wire.

6. An electrical stimulation device for applying electrical stimulus to parts of a living body according to claim 5, wherein the ribbon wire forming each applicator has about 40 conductors.

7. An electrical stimulation device for applying electrical stimulus to parts of a living body according to claim 6, wherein the length of the ribbon wire forming each applicator is about 9 inches.

8. An electrical stimulation device for applying electrical stimulus to parts of a living body according to claim 7, wherein the conductors are formed of a silver-copper alloy.

9. An electrical stimulation device for applying electrical stimulus to parts of a living body according to claim 1, additionally including straps connected to the applicators to strap the applicators against the living body and hold the electrodes in contact with the living body during treatment.

10. An electrical stimulation device for applying electrical stimulus to parts of a living body comprising:
   a pair of applicators adapted to each contact the living body, said applicators each including electrically conductive material covered by electrically insulating material whereby the electrically conductive material is separated from the living body by the electrically insulating material when the applicators contact the living body;
   a signal generator having a pair of output terminals and adapted to generate an electrical signal between the output terminals to be applied to the living body through the applicators, wherein the electrical signal has a voltage in the range of 10,000 to 20,000 volts; and
   electrical conductors connecting respective separate terminals of the pair of signal generator terminals to respective separate applicators of the pair of applicators to supply the electrical signal generated by the signal generator to the applicators.

11. An electrical stimulation device for applying electrical stimulus to parts of a living body according to claim 10, wherein the power applied by the signal generator to the applicators is in the range of about 5 to about 120 watts.

12. An electrical stimulation device for applying electrical stimulus to parts of a living body according to claim 11, wherein the applicators are adapted to apply power to the living body with a power density up to about one watt per square centimeter.

13. An electrical stimulation device for applying electrical stimulus to parts of a living body according to claim 10, wherein the power applied by the signal generator to the applicators is in the range of about 1 to about 120 watts.

14. An electrical stimulation device for applying electrical stimulus to parts of a living body according to claim 10, wherein the applicators are adapted to apply power to the living body with a power density up to about one watt per square centimeter.

15. An electrical stimulation device for applying electrical stimulus to parts of a living body comprising:
   a pair of applicators adapted to each contact the living body, said applicators each including electrically conductive material covered by electrically insulating material whereby the electrically conductive material is separated from the living body by the electrically insulating material when the applicators contact the living body;
   a signal generator having a pair of output terminals and adapted to generate an electrical signal between the output terminals to be applied to the living body through the applicators, wherein the electrical signal is a series of positive electrical pulses and the frequency of the pulses is in the range of 1 to 10,000 Hertz; and
   electrical conductors connecting respective separate terminals of the pair of signal generator terminals to respective separate applicators of the pair of applicators to supply the electrical signal generated by the signal generator to the applicators.

16. An electrical stimulation device for applying electrical stimulus to parts of a living body according to claim 15, wherein the duration of each positive electrical pulse is about 1 millisecond.

17. An electrical stimulation device for applying electrical stimulus to parts of a living body, comprising:
   a pair of applicators adapted to each contact the living body, said applicators each formed from a length of insulated, multiconductor ribbon wire having electrically conductive material covered by electrically insulating material whereby the electrically conductive material is separated from the living body by the electrically insulating material when the applicators contact the living body;
   a signal generator having a pair of output terminals and adapted to generate an electrical signal between the output terminals to be applied to the living body through the applicators; and
   electrical conductors connecting respective separate terminals of the pair of signal generator terminals to respective separate applicators of the pair of applicators to supply the electrical signal generated by the signal generator to the applicators.

18. An electrical stimulation device for applying electrical stimulus to parts of a living body according to claim 17, wherein the applicators are adapted to apply power to the living body with a power density up to about one watt per square centimeter.

19. An electrical stimulation device for applying electrical stimulus to parts of a living body according to claim 17, additionally including straps connected to the applicators to strap the applicators against the living body and hold the electrodes in contact with the living body during treatment.

20. An electrical stimulation device for applying electrical stimulus to parts of a living body according to claim 12 wherein the power applied by the signal generator to the applicators is in the range of about 5 to about 120 watts.

* * * * *